United States Patent [19]

Sasse et al.

[11] 4,235,960

[45] Nov. 25, 1980

[54] COMPETITIVE ENZYME-LINKED IMMUNOASSAY

[75] Inventors: Edward A. Sasse, Brookfield; Donald E. Yorde, Milwaukee, both of Wis.

[73] Assignee: The Medical College of Wisconsin, Inc., Milwaukee, Wis.

[21] Appl. No.: 820,286

[22] Filed: Jul. 29, 1977

[51] Int. Cl.$^2$ ............................................. G01N 31/14
[52] U.S. Cl. .......................................... 435/7; 424/12; 435/28; 435/177
[58] Field of Search ................... 195/103.5 A; 424/12; 435/7, 28, 177

[56] References Cited

U.S. PATENT DOCUMENTS

| | | | |
|---|---|---|---|
| 3,773,625 | 11/1973 | Sternberger et al. | 195/103.5 A |
| 3,879,262 | 4/1975 | Schuurs et al. | 195/103.5 A X |
| 4,002,532 | 1/1977 | Weltman et al. | 424/12 |
| 4,021,534 | 5/1977 | Lafontaine | 424/12 |
| 4,024,235 | 5/1977 | Weetall et al. | 195/103.5 A X |
| 4,034,074 | 7/1977 | Niles | 424/12 |
| 4,048,298 | 9/1977 | Niswender | 424/12 |

OTHER PUBLICATIONS

Yorde, et al., Competitive Enzyme-Linked Immunoassay with Use of Soluble Enzyme/Antibody Immune, Complexes For Labeling I. Measurement of Human Choriogonadotropin. Clinical Chemistry vol. 22, No. 8 1976 (pp. 1372–1377).

Hinton, et al., The Unlabeled Antibody Enzyme Method of Immunohistochemistry. The Journal of Histochemistry and Cytochemistry, vol. 21, No. 11, 1973 (pp. 978–998).

*Primary Examiner*—David M. Naff
*Attorney, Agent, or Firm*—Quarles & Brady

[57] ABSTRACT

A competitive enzyme-linked immunoassay for a soluble analyte in which the analyte in the unknown sample and the same analyte attached to a solid phase (immunosorbent) compete for a selected quantity of a soluble first antibody to the substance; a second or bridging antibody is then linked to any first antibody linked to the immunosorbent as a result of the competitive reaction, following which a soluble enzyme/antibody immune complex is linked to bridging antibody on the immunosorbent. The enzymatic activity associated with the thusly-formed enzyme-immunosorbent complex or with the non-immunosorbent fraction of enzyme is measured to determine the presence and/or concentration of analyte in the unknown sample.

9 Claims, No Drawings

COMPETITIVE ENZYME-LINKED IMMUNOASSAY

BACKGROUND OF THE INVENTION (1) Field

The general field of our present invention is the art of quantitative measurement of analytes such as immunogens or haptens dissolved in biological fluids.

(2) Prior Art

Competitive protein-binding assays and radioimmunoassays are used for measurements of substances in biological fluids which require that the substance be labeled with a radioisotope in order to achieve the desired specificity and sensitivity.

Other assay methods use an enzyme label to obviate problems of radioactivity labeling. One type of enzyme labeling method uses a competitive immunoassay between unlabeled antigen and the antigen labeled with an enzyme for an antibody bound to an immunosorbent; Engvall and Perlmann were among the first to disclose this technique in their paper entitled Enzyme-Linked Immunosorbent Assay, ELISA, 8 *Immunochemistry* 871 (1971), and others have subsequently published variations of their general approach. A second type of enzyme labeling method employs antibody (rather than antigen) labeled with enzyme and antigen covalently bound to an immunosorbent; antigen in the unknown sample is assayed in a non-competitive reaction with the enzyme labeled antibody, followed by separation of antigen/labeled antibody complexes. Masseyeff and Maiolini have co-authored articles on this technique published in 19 *Biomedicine* 314 (1973), 6 *J. Immuno. Methods* 355 (1975) and 8 *J. Immuno. Methods* 223 (1975). A third type of enzyme immunoassay as reported by Rubenstein et al in 47 *Biochem. Biophys. Res. Commun.* 846 (1972), see also U.S. Pat. No. 3,877,837 to Rubenstein et al, utilizes enzyme covalently linked to the analyte. In the case of hapten assay, antibody to the hapten will bind the hapten/enzyme conjugate and sterically inhibit enzymatic activity. The hapten to be assayed by this technique will compete for antibody with the hapten/enzyme conjugate, thereby decreasing the inhibition of enzyme activity, and the subsequent increase in enzymatic activity will be proportional to the original amount of hapten present.

Prior art methods discussed briefly above are described in greater detail in Yorde et al, Competitive Enzyme-Linked Immunoassay etc., 22 *Clinical Chemistry* 1372 (1976), which paper is hereby incorporated by reference as to its discussion of the prior art and our present invention. Voller et al review various immunoassays in their article Enzyme Immunoassays in Diagnostic Medicine, 53 Bull. World Health Organ. 55 (1976).

Our new immunoassay for soluble immunogens and haptens is believed to offer advantages over the prior methods referred to above, as discussed in detail in the ensuing description.

SUMMARY OF THE INVENTION

According to our present immunoassay, an antibody bonded to an immunosorbent is linked to a bridging second antibody and then to an enzyme/antibody immune complex; the activity of immunosorbent-bound enzyme or non-immunosorbent bound enzyme is measured and is related to the concentration of analyte in the sample.

A more detailed summary of a suitable procedure for the quantitative measurement of a soluble immunogen or hapten analyte in a biological solution in accordance with the present invention includes the steps of:

(I) forming a mixture containing (1) a sample solution suspected of containing the analyte, (2) an insoluble solid immunosorbent having the analyte linked thereto, and (3) a selected quantity of first antibody for the analyte, and thereafter
 (a) incubating the mixture to enable the first antibody to react with analyte in the solution under analysis and analyte linked to the solid immunosorbent, and
 (b) separating the solid immunosorbent from the mixture;

(II) mixing the solid immunosorbent from step (I) with a solution containing a heterologous bridging antibody, and
 (a) incubating the mixture to link bridging antibody molecules to any first antibody molecules linked to the solid immunosorbent, and
 (b) separating the solid immunosorbent from the mixture;

(III) mixing the solid immunosorbent from step (II) with a soluble antibody-enzyme immune complex, and
 (a) incubating the mixture to link antibody-enzyme immune complex to bridging antibody molecules on the immunosorbent,
 (b) separating the solid immunosorbent, and
 (c) releasing enzyme coupled to the immunosorbent and determining the activity of released enzyme, or measuring the activity of enzyme while coupled to the immunosorbent, to thereby ascertain the presence of analyte in the sample solution.

The enzymatic activity associated with the thusly-formed enzyme-immunosorbent complex is measured since it is inversely proportional to the concentration of analyte in the unknown sample since the amount of first antibody coupled to the immunosorbent is inversely proportional to the amount of analyte in the unknown sample and the amount of bridging antibody and enzyme/antibody immune complex coupled to the solid immunosorbent is directly proportional to the amount of first antibody bound to the immunosorbent.

Our present immunoassay differs from prior techniques in that it is a competitive assay for substances in solution and involves noncovalent linkage of the enzyme label, i.e., soluble enzyme/antibody immune complexes for labeling. Other enzymatic immunoassays have depended upon covalent enzyme labeled antigen or antibody. A number of significant advantages accrue from the present immunoassay that will be discussed in detail hereinafter, but which briefly include: the elimination of prior covalent coupling of the enzyme label to the analyte or antibody; the ability to use a selected bridging antibody and antibody-enzyme immune complex as reagents for different specific antigen assays; and the ability to assay for both low and high molecular weight analytes.

A principal object of this invention is to provide an immunoassay method which does not depend upon covalent coupling of analyte or antibody to enzyme; another is to provide a sensitive immunoassay; still another is to provide an immunoassay which can employ a few reagents to analyze for a variety of specific analytes; and a further principal object is the provision of an immunoassay applicable to both low and high molecular weight analytes. A more specific object is to provide the particular methods and products as hereinafter claimed.

DESCRIPTION OF THE SPECIFIC EMBODIMENTS

The present invention relates to a competitive enzyme-linked immunoassay for the quantitative measurement and detection of very small concentrations of a wide range of soluble analytes. In the assay method a limited amount of a first antibody, which is specific for the analyte, is added to a sample suspected of containing the analyte and an insoluble solid immunosorbent having the analyte coupled thereto. The binding of the antibody to the analyte-immunosorbent is competitively inhibited by the free analyte in the sample. The amount of the antibody bound to the immunosorbent is measured by an enzymatic technique in which a heterologous bridging antibody and a soluble antibody-enzyme immunocomplex are applied in sequence. The analyte concentration is measured by measuring the activity of the enzyme bound to the immunosorbent which is inversely proportional to the concentration of the analyte in the original sample; alternatively, analyte concentration can be measured by measuring the activity of enzyme that is not bound to the immunosorbent which is directly proportional to the analyte concentration.

The preferred manner of measuring the enzyme activity employs spectrophotometric procedures. However, in some instances other methods of determination may be preferable. Among the other methods that can be used are fluorimetry and nephelometry.

The analytes which may be assayed are those which may be classified as follows:

(a) Immunogens which are compounds which when introduced into a vertebrate will result in the formation of antibodies. Representatives of the immunogens are proteins, glycoproteins and nucleoproteins, such as peptide hormones, serum proteins, complement proteins, coagulation factors, and viral or bacterial products.

(b) Haptens which are compounds which when bound to an immunogenic carrier and introduced into a vertebrate will elicit formation of antibodies specific for the hapten. Representative of the haptens are steroids such as estrogens and cortisones, low molecular weight peptides, other low molecular weight biological compounds, drugs, industrial pollutants, flavoring agents, food additives, and food contaminants, and/or their metabolites or derivatives.

Representative of specific analytes that can be measured by the practice of the present invention are the following:

| (a) haptens | |
|---|---|
| Morphine and Opiates | Testosterone |
| Barbiturates | Cortisol |
| Methadone | Estrogens |
| Diphenylhydantoin | Progesterone |
| Phenobarbital | Thyroxine |
| Primidone | Triiodothyronine |
| Digoxin | Folates |
| Codeine | |
| (b) immunogens | |
| Ferritin | Vasotocin |
| Insulin | Vasopressin |
| Placental lactogen | Somatotropin |
| Thyrotropin | Prolactin |

| -continued | |
|---|---|
| $\alpha_1$-Fetoprotein | Melanotropin |
| $\alpha_2$ H-Globulin | Lutropin |
| Haptoglobin | Lipotropin |
| Hepatitis B surface antigen | Oxytocin |
| Carcinoembryonic antigen | Gonadotropin |
| Albumin | Follitropin |
| Immunoglobulins (A,D,G,E,M) | Corticotropin |
| Gastrin | Choriomamotropin |
| Thymopoietin | Choriogonadotropin |
| Somatomedin | Thyroliberin |
| Secretin | Somatostatin |
| Relaxin | Somatoliberin |
| Proangiotensin | Prolactostatin |
| Parathyrin | Prolactoliberin |
| Pancreozymin | Melanostatin |
| Kallidin | Melanoliberin |
| Glucagon | Luliberin |
| Gastrin sulfate | Gonadoliberin |
| Erythropoietin | Folliberin |
| Calcitonin | Corticoliberin |
| Bradykinin | Fibrinogen |
| Angiotensin | Factor VIII |
| | Antithrombin III |

The above list is obviously incomplete as the method of the present invention can be used to assay for any analyte that forms an antibody that can be used in the assay, and it can be used to assay for an antibody analyte.

The first antibody, which is specific for the analyte, may be produced by introducing the analyte, if it is an immunogen, into a living vertebrate. The antibodies which are produced in response to the introduction of the immunogen are proteins that coat the immunogen and detoxify it, precipitate it from solution, or simply combine with it. The antibody protein forms a coat which is geometrically arranged so that the immunogen fits the spatial arrangement of the protein. In the case of a hapten an extra step is involved in preparing the antibody. The hapten must be conjugated to an immunogenic carrier prior to introduction into a living vertebrate. The method of preparing the antibodies from non-immunogens (haptens) is well known to those skilled in the art.

The first antibodies preferred for use in the present invention are those prepared from rabbit. Representative of other first antibodies are those prepared from or occur in the following species of animals: (a) hamster, (b) goat, (c) chicken, (d) rat, (e) guinea pig, (f) sheep, (g) horse, (h) mouse, and (i) human.

The heterologous bridging antibody is antisera directed against the immunoglobulins from the same species as the first antibody. The preferred bridging antibody is goat anti-rabbit immunoglobulin G, which will recognize any rabbit immunoglobulin G and bridge between a first rabbit antibody and another rabbit antibody in the antibody-enzyme immunocomplex. Both the bridging antibody and the soluble antibody-enzyme immumocomplex can be used for a wide variety of different analyte assays.

The preferred bridging antibody is the previously stated goat anti-rabbit immunoglobulin G which is commercially available. Representative of other linking antibodies are those heterologous anti-immunoglobulins that may be produced from the following species of animals: (a) rabbit, (b) chicken, (c) rat, (d) guinea pig, (e) sheep, (f) hamster, (g) mouse, (h) horse.

The antibody-enzyme immunocomplex serves as the labeling agent. The preparation and use of soluble antibody-enzyme complexes has been described by Sternberger et al in 18 J. Histochem. Cytochem. 315 (1970). The soluble immunocomplex preferred for use in the invention is rabbit anti-peroxidase/horseradish peroxidase, which is commercially available. The preferred immunocomplex can be used for a great number of different types of assays as many different rabbit antibodies are commercially available. The antibody portion of the antibody-enzyme immunocomplex must be either of the same species as the first antibody or of a cross reactive species.

Representative of other soluble antibody-enzyme immunocomplexes are those using antibodies from goat, hamster, chicken, rat, guinea pig, sheep, mouse or baboon and enzymes such as oxidases, catalases, esterases and dehydrogenases or any other enzyme that forms a soluble immune complex with the selected antibody and exhibits measurable enzyme activity in our present method.

The immunosorbent materials that can be used in the assay are those materials which are insoluble under conditions of the assay and to which the analyte can be suitably coupled or attached. A useful immunosorbent for the assay is agarose in bead form; other types of materials including (a) other carbohydrates such as dextran and cellulose, (b) plastics such as polystyrene, polycarbonate, polypropylene and polyamide, (c) inorganic materials such as glass, silica gel and aluminum oxide, and (d) cross-linked proteins might be employed. These materials may be in the form of particles, tubes and plates in various shapes and sizes. If suitable, the use of dense beads or other physical forms which do not require centrifugation is helpful. In some instances the analyte may be coupled chemically to the immunosorbent and in others it may be incorporated into a material to be coated onto the surface of the immunosorbent. In general, any method of attaching the analyte to the immunosorbent that results in a usable analyte-immunosorbent complex may be used.

EXAMPLE 1

The following description will serve to illustrate the competitive assay of the present invention for the measurement of an immunogen. Soluble human choriogonadotropin (HCG), the analyte in a test sample, competes with HCG covalently bound to an immunosorbent for binding the rabbit-antiHCG-antibody, the first antibody. The amount of the antiHCG-antibody available for binding to the HCG/immunosorbent will be diminished by the amount of free HCG in the original sample. The amount of antiHCG-antibody bound to the immunosorbent is then determined by immunologically linking enzyme to this complex. Goat anti-rabbit immunoglobulin G (GARIgG) is used as a bridge between the rabbit antiHCG and soluble rabbit anti-peroxidase/peroxidase complex (PAP). Thus, horseradish peroxidase through additional immune reactions becomes the enzymatic label on the immunosorbent. The peroxidase is subsequently released from the immunosorbent to facilitate the enzymatic assay. The peroxidase activity is inversely proportional to the concentration of the soluble HCG in the original sample as prescribed in competitive protein binding principles.

The series of reactions that occur, are as follows:

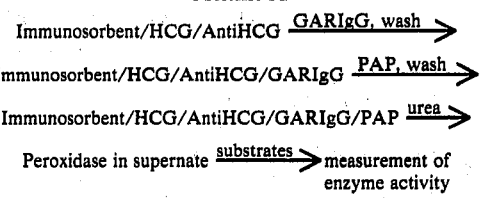

Peroxidase in supernate $\xrightarrow{\text{substrates}}$ measurement of enzyme activity (a) Purification of HCG (Analyte)

Commercial human choriogonadotropin (HCG) (A.P.L. brand; Ayerst Laboratories, Inc., New York, N.Y. 10017) was fractionated by ion-exchange chromatography on diethylaminoethyl-Bio-Gel A (100–200 mesh; Bio-Rad Laboratories, Richmond, Calif. 94804) as described by 224 Bahl, J. Biol. Chem., 567 (1969). The eluted fraction corresponding to HCG was further purified by gel filtration on Sephadex G-150 (Pharmacia, Inc., Piscataway, N.J. 08854). The Sephadex-purified HCG fraction was collected, dialyzed exhaustively against distilled water, and lyophilized.

(b) Coupling Analyte to Immunosorbent

The purified HCG (60 mg) was coupled to the immunosorbent agarose. (Sepharose 4B-Pharmacia) by the method of March et al. 60 Anal. Biochem., 149 (1974). The agarose beads (20 ml packed gel) were activated at 24° C. with 1 g of cyanogen bromide in 0.5 ml of acetonitrile. The HCG/Sepharose was stored at 4° C. in 100 ml of sodium phosphate-buffered saline (10 mmol/liter phosphate, 0.14 mol/liter NaCl, pH 7.4) containing 0.1 g of $NaN_3$ per liter as preservative. Recovery experiments indicated that about 1.5% of the added hormone was coupled to the Sepharose 4B, to give about 45 μg (or 225 int. units) of HCG per milliliter of packed gel, or 0.9 μg (4.5 int. units) per 100 μl of gel suspension as used in the assay. This material is stable for at least six months when stored at 4° C.

(c) Preparation of Enzyme/Antibody Immune Complex

Horseradish peroxidase (Sigma VI, lot No. 44C-9570; Sigma Chemical Co., St. Louis, Mo. 63178) was dissolved in physiological saline and emulsified with complete Freund adjuvent (Difco Labs, Detroit, Mich. 48232) and injected subcutaneously into New Zealand white rabbits. Five injection sites were used, with a total dose of 2.5 mg per animal. An identical second injection was administered after two weeks and the rabbits were bled at irregular intervals from four to 12 weeks after the first injection. The sera were pooled and stored at −70° C. The soluble immune complexes of peroxidase and anti-peroxidase were prepared as described by Sternberger *Immunocytochemistry* (Prentice-Hall, 1974) p. 129. The soluble complexes are stable for at least one year, stored at −70° C.

(d) Comparison

A double-antibody radioimmunoassay was used, for comparison purposes, as described by Midgley, 79 *Endocrinology*, 10 (1966). Commercially available rabbit anti-HCG antiserum (final dilution 1/180,000; lot No. 1547; Ortho Laboratories, Raritan, N.J. 08869) was the first antibody, goat anti-rabbit-γ-globulin (lot No. 1257: ICN Pharmaceuticals, Inc., Cleveland, Ohio 44128) the linking antibody. The Second International Reference Preparation for HCG, used as a standard, was kindly supplied by the World Health Organization. Highly purified HCG (CR-115) for iodination was provided by the National Institute of Child Health and Human Development and the National Institute of Arthritis, Metabolic and Digestive Disease, NIH. $Na^{125}I$ for radio-iodination was purchased from New England Nuclear Corp., Boston, Mass. 02118.

(e) Competitive Enzyme-Linked Immunoassay

HCG stock standard was prepared from A.P.L. brand HCG (control No. 1VSB) after exhaustive dialysis against phosphate-buffered saline. The concentration of HCG was determined by the radioimmunoassay procedure, with the International Reference Preparation of HCG as a standard. Working standards of 1 to 50 int. units per milliliter were prepared by diluting the stock standard with phosphate-buffered saline containing 10 g of bovine serum albumin (Armour Pharmaceutical Co., Chicago, Ill. 60650; Fraction V:BSA) per liter.

HCG/Sepharose, 100 μl (containing about 0.9 μg of HCG), was added to 1.0 ml of soluble HCG solution (standard or sample), followed by the addition of 100 μl of rabbit anti-HCG (lot No. 1515; ICN Pharmaceuticals, Inc.) at a dilution of 1/1000. The mixture was incubated for 2 hours at room temperature with constant stirring (glass-coated magnetic stirring bar). The immunosorbent beads were washed three times each with about 10 ml of phosphate-buffered saline by suspension, centrifugation (1100× g, 5 min.) and aspiration of the supernate down to a constant volume of 0.5 ml. After the final wash, the beads were suspended in 1.0 ml of a 1/400 dilution of goat anti-rabbit immunoglobulin G (lot No. 2072; ICN Pharmaceuticals, Inc.). After a 20 minute incubation at room temperature, the HCG/Sepharose was washed as described above. The residual bead suspension was then treated with 0.5 ml of a 1/50 dilution of the anti-peroxidase/peroxidase preparation for a similar 20 minute incubation and was washed four times. The dilutions of goat anti-rabbit immunoglobulin G and anti-peroxidase/peroxidase were made with the phosphate-buffered saline/albumin diluent. After aspiration of the last wash, 2.0 ml of 6 mol/liter urea was added to the tube, and the mixture was incubated for 10 minutes with constant stirring. After centrifugation, 0.4 ml of the supernate was transferred to a test tube containing 1.6 ml of 10 mmol/liter phosphate buffer (pH 6.0), followed by 2.0 ml of peroxidase substrate (30 mg/liter $H_2O_2$ and 80 mg/liter o-dianisidine) for color development, as described by 54 Avrameas and Guilbert, Biochimie, 837 (1972). After exactly 10 minutes at room temperature, the reaction was stopped with 0.1 ml of 5 mol/liter HCl and the absorbance was measured at 400 nm on a Spectronic 100 spectrophotometer (Bausch & Lomb, Inc., Rochester, N.Y. 14625).

The initial incubation time for immunosorbent, free antigen, and antibody was set at 2 hours, to limit appropriately the total time required for the procedure. The concentration of first antibody to be used for the assay was determined by testing serial dilutions of anti HCG under zero standard conditions, the object being to find the limiting concentration that will bind all the available sites on the HCG/Sepharose. The 1/1000 dilution of the anti HCG preparation was considered optimal, and was used in subsequent competitive-binding assays with this same volume of HCG/Sepharose (100 μl). The amount of goat anti-rabbit immunoglobulin G and anti-peroxidase/peroxidase should be in excess for the experimental conditions used; both were tested in this system for optimization. The highest dilutions possible were chosen that would give the maximum final absorbance values under zero standard conditions and with the proposed incubation times. Longer incubation times with the proposed amounts of goat anti-rabbit immunoglobulin G and anti-peroxidase/peroxidase did not increase the final absorbance readings.

As the amount of added soluble HCG was increased, the intensity of the color reaction decreased progressively. The working range of the assay was from 1 to 50 int. units/ml of sample. Typical absorbances obtained under the prescribed experimental conditions ranged from 1.5 for the zero standard to 0.25 for the 50 int. units/ml standard. The dialyzed commercial HCG used as a standard was equivalent to the International Reference Preparation of HCG by radioimmunoassay. Conversely, when the reference material was assayed by the method of the present invention, the expected values were obtained. The serum from a patient with choriocarcinoma was diluted to test for parallelism. The curves for standard and choriocarcinoma serum were found to coincide. The within-run coefficient of variation of the method, as determined by 24 replicate analyses of a 4 into unit/ml standard, was 9.6%. As a preliminary evaluation of the clinical applicability of the assay method, HCG was measured in five sera and five urine samples and the results were found to be comparable to results obtained by radioimmunoassay. The least squares regression line of the radioimmunoassay results plotted vs. the Example 1 results had a slope of 0.90 and an intercept of −1 int. units/ml. The correlation coefficient for these points was 0.989 with p less than 0.0005.

EXAMPLE 2

The following description will serve to illustrate the competitive assay of the present invention for the measurement of a hapten. Soluble testosterone, the analyte in a test sample, competes with testosterone covalently bound to an immunosorbent for binding the rabbit-antitestosterone-antibody, the first antibody. The amount of the antitestosterone-antibody available for binding to the testosterone/immunosorbent will be diminished by the amount of free testosterone in the original sample. The amount of antitestosterone-antibody bound to the immunosorbent is then determined by immunologically linking enzyme to this complex. Goat anti-rabbit immunoglobulin G (GARIgG) is used as a bridge between the rabbit antitestosterone and soluble rabbit anti-peroxidase/peroxidase complex (PAP). Thus, horseradish peroxidase through additional immune reactions becomes the enzymatic label on the immunosorbent. The peroxidase activity on the immunosorbent is then measured without being released from the immunosorbent. The peroxidase activity is inversely proportional to the concentration of the soluble testosterone in the original sample as prescribed in competitive protein binding principles.

The series of reaction that occur, are as follows:

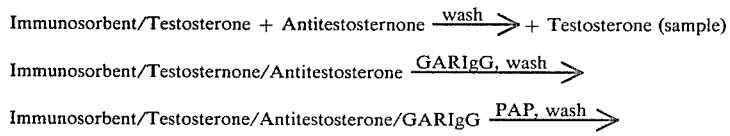

-continued

Immunosorbent/Testosterone/Antitestosterone/GARIgG/PAP $\xrightarrow{\text{substrates}}$
peroxidase activity measured on immunosorbent (a) Coupling of Analyte to Immunosorbent (1) Preparation of testosterone-3-0-carboxymethyl oxime Commercial testosterone (Sigma Chemical Co., St. Louis, Mo.) was used to prepare the 3-0-carboxymethyl oxime derivative of testosterone. This derivative was prepared according to the method of Erlanger, B. F., 228 *J. Biol. Chem.*, 713 (1957).

A solution containing 1.0 g of testosterone and 1.07 g of 0-carboxymethyl hydroxylamine in 200 ml of ethanol was made alkaline by addition of 20 ml of 5 g/dl NaOH and refluxed for 1.5 hours. The solution was heated for an additional 30 minutes without the refluxing condenser. The solution was cooled to room temperature, diluted with 150 ml of water and extracted twice with 100 ml of ether. The alkaline aqueous phase was acidified with three ml of concentrated hydrochloric acid and the resulting precipitate was extracted with 100 ml of ether. The ether extract was washed five times with 30 ml of water and evaporated to dryness. The crude product was recrystallized three times in 50% (v/v) benzene-petroleum ether mixture. The melting point of the testosterone-3-0-carboxymethyl oxime (T-3-Oxime) was 176°-179° C., and the ultra-violet spectrum of the solution in 0.05 M Tris buffer (pH 8.5) was maximal at 250 nm. The recrystallized testosterone-3-0-carboxymethyl oxime was used for further conjugation to gelatin.

(2) Synthesis of testosterone-3-gelatin (T-3-gelatin)

T-3-gelatin was prepared by a modification of the method of Chen, J. C. et al, 17 *Clin. Chem.* 581 (1971).

200 mg of T-3-oxime and 0.2 ml of tributylamine were dissolved in 6 ml of dioxane. This solution was cooled to 4° C. and 0.1 ml of isobutyl chlorocarbonate was added. The mixture was allowed to react for 20 min at 4° C. with continuous stirring and then added to a cooled solution of 1 g of gelatin in 50 ml of water and 25 ml of dioxane followed by the addition of 1 ml of 1 N NaOH with stirring. After 1 hour, 0.5 ml of 1 N NaOH was added, and stirring and cooling were continued for an additional 2 hours. The solution was dialyzed overnight against distilled water with two changes of water. The resulting suspension after dialysis containing T-3-gelatin was stored at −20° C. for further use.

(3) Coupling of T-3-gelatin to Sepharose 4B

T-3-gelatin was coupled to CN-Br activated Sepharose 4B (Pharmacia, Inc. Piscataway, N.J.) according to the specifications described by Pharmacia. Two milliliters of T-3-gelatin suspension was dissolved in 8 ml of water and 1 ml of 0.5 M NaHCO$_3$. This solution was added to 1.5 g of activated Sepharose 4B which had been washed four times with 0.001 N HCl. After 2 hours of inversion mixing at room temperature on a tube rotator, the supernate was removed and the remaining precipitate was reacted with 10 ml of 1 M ethanolamine pH 9.0 for 2 hours using rotation inversion mixing. Three washing cycles were used to remove noncovalently absorbed T-3-gelatin on the beads, each cycle consisting of a wash at pH 4 (0.1 M acetate buffer containing 1 M NaCl) followed by a wash at pH 8 (0.1 M borate buffer containing 1 M NaCl). The beads were further washed three times with sodium phosphate buffered saline (10 mmol/liter phosphate, 0.14 mol/liter NaCl, pH 7.4) and diluted 1:5 after the last washing. The resulting testosterone preparation immunosorbent was diluted 1:100 for use in the assay. The preparation is stable for 2–3 months at 4° C. Undiluted packed T-3-gelatin-S-4B immunosorbent contained 50–100 ng testosterone/ml beads as determined by the radioimmunoassay method of Chen, J. C. et al, 17 *Clin. Chem.* 581 (1971).

(b) Preparation of Enzyme/Antibody Immune Complex

Horseradish peroxidase (Sigma VI, Lot No. 44C-9570; Sigma Chemical Co., St. Louis, Mo. 63178) was dissolved in physiological saline and emulsified with complete Freund adjuvent (Difco Labs, Detroit, Mich. 48232) and injected subcutaneously into New Zealand white rabbits. Five injection sites were used, with a total dose of 2.5 mg per animal. An identical second injection was administered after two weeks and the rabbits were bled at irregular intervals from four to 12 weeks after the first injection. The sera were pooled and stored at −70° C. The soluble immune complexes of peroxidase and anti-peroxidase were prepared as described by Sternberger. The soluble complexes are stable for at least a year, stored at −70° C.

(c) Comparison

A radioimmunoassay was used for comparison purposes as described by Chen, J. C. et al, 17 *Clin. Chem.* 581 (1971). Commercially available rabbit anti-testosterone antisera (Wien Laboratories, Succosanna, N.J.) was purchased as lyophilized material. Each vial was reconstituted with 5 ml of phosphate saline albumin buffer (0.025 M Na$_2$HPO$_4$, 0.06 g/dl albumin, 0.85 g/dl NaCl, pH 6.8) before use. Tritium labeled testosterone ($^3$H-testosterone, specific activity, 40 Ci/mmole, New England Nuclear, Boston, Mass.) was diluted appropriately so that the total activity in the in the assay tubes was approximately 15,000 counts per minute under the experimental conditions of the assay procedure.

(d) Competitive Enzyme-Linked Immunoassay

Testosterone (Sigma Chemical Co., St. Louis, Mo.) stock standard was prepared by volumetric dissolution in 95% ethanol. Working Standards of 1.0 to 10 ng/ml were prepared by diluting the stock standard with appropriate volumes of 95% ethanol. One-tenth milliliter amounts of working standards were added to individual tubes and allowed to evaporate to dryness.

Appropriate volumes of biological fluid samples (male serum, 0.1 ml; female serum 1.0 ml; etc.) were extracted with 15 ml of chloroform. A 10 ml aliquot of the chloroform extract from each sample was transferred to an individual tube and evaporated to dryness.

To all the tubes (standards and unknowns), 1.0 ml of phosphate buffered saline (10 mmol/liter phosphate, 0.14 mol/liter NaCl, pH 7.4) was added followed by the addition of 0.5 ml of the working testosterone immunosorbent (T-3-gelatin-Sepharose 4B) preparation, followed by the addition of 0.2 ml of first antibody (lyophilized rabbit antitestosterone Bio-RIA, Division of the Institute of Bio-Endocrinology Inc., Montreal, Quebec, Canada, vials were reconstituted with 10.0 ml of water). The mixture was incubated for 20 minutes at room temperature with constant stirring (teflon-coated magnetic stirring bar). The immunosorbent beads were washed twice each with about 10 ml of phosphate buffered saline containing 0.1% Triton X-100 by suspension, centrifugation (1100× g, 3 min) and aspiration of the supernate down to a constant volume of about 0.5 ml. After the second wash, the beads were resuspended in 1.0 ml of a 1/800 dilution of second antibody (goat anti-rabbit immunoglobulin G, Lot #5334 ICN Pharmaceuticals, Inc.) The mixture was incubated for 10 minutes at room temperature, after which the immunosorbent beads were washed again as described above. The residual bead suspension was then treated with 0.5 ml of a 1/200 dilution of the anti-peroxidase/peroxidase preparation for a 10 minute incubation, followed by three washes. The dilutions of goat anti-rabbit immunoglobulin G and anti-peroxidase/peroxidase were made with phosphate buffered saline containing 0.1 g/dl gelatin.

After aspiration of the last wash, 2.0 ml of peroxidase substrate solution (30 mg/liter $H_2O_2$, 160 mg/liter 0-dianisidine in 0.01 M phosphate buffer, pH 6) was added directly to the immunosorbent beads with constant stirring and the mixture was incubated for exactly 10 minutes for color development. The reaction was stopped with 0.2 ml of 5 N HCl and centrifuged. The absorbance of the supernate was measured at 400 nm on a Gilford Instruments Model 300-N spectrophotometer.

The incubation times and reagent concentrations were established in an effort to limit the total time required for the procedure consistent with the sensitivity levels desired. The concentration of first antibody to be used for the assay was determined by testing different dilutions of anti-testosterone under zero standard conditions, the object being to find the limiting concentration that will bind all the available sites on the testosterone/immunosorbent. The amount of goat anti-rabbit immunoglobulin G and anti-peroxidase/peroxidase should be in excess for the experimental conditions used; both were tested in this system for optimization. The highest dilutions possible were chosen that would give the maximum final absorbance values under zero standard conditions and with minimum incubation times. Longer incubation times with the proposed amounts of goat anti-rabbit immunoglobulin G and anti-peroxidase/peroxidase did not increase the final absorbance readings.

As the amount of added soluble testosterone was increased, the intensity of the final color reaction decreased progressively. The working range of the assay as described was from 1 to 10 ng/ml of testosterone utilizing a 0.1 ml sample size, i.e., 0.1 to 1 ng/tube. Typical absorbances obtained under the prescribed experimental conditions ranged from 1.6 for the zero standard to 0.7 for the 10 ng/ml standard. As a preliminary evaluation of the clinical applicability of the assay method, testosterone was measured in ten patient serum samples and the results were found to be comparable to results obtained by radioimmunoassay. The least squares regression line of our assay results plotted vs the radioimmunoassay results had a slope of 0.97 and an intercept of 0.3 ng/ml. The correlation coefficient for these points was 0.954 with p less than 0.001.

Although various conditions such as quantity, time and temperature as illustrated in Examples 1 and 2 may be varied for different analytes, those skilled in the art will have no difficulty in modifying our assay for use with a new analyte. The assay will normally be conducted at moderate temperatures, usually in the range of 10° to 50° C. at pH of about 5 to 10. In general, the assay can be adapted for a specific analyte by the following procedure:

(1) obtain or prepare a purified form of the analyte;
(2) obtain or prepare a suitable antibody for said analyte;
(3) prepare a suitable insoluble immunosorbent;
(4) using a test sample of zero and known concentrations of the analyte and varied amounts of analyteimmunosorbent establish the conditions under which competition for the antibody exists between the analyte in the solution and the insoluble analyte-immunosorbent;
(5) establish optimum amounts of bridging antibody and antibody-enzyme immune complex, preferably an excess of each is used to ensure complete reaction; and
(6) when conditions for competition have been set, select a suitable method of measuring the enzymatic activity for the range of concentrations of analyte desired to be measured in the unknown sample.

Once the conditions for the assay and given analyte have been set kits can be assembled containing necessary reagents and instructions for performing the assay. Such kits will usually include separate containers containing measured amounts of the first antibody which is specific for the analyte; a suitable analyte-immunosorbent; a bridging antibody; and the soluble enzyme/antibody immune complex for labeling. If the enzyme activity is to be measured by color development, the kit will also contain the necessary color development reagents and/or color charts and directions for their use. The kits may also contain the necessary tubes and vessels for performing the several reactions if the containers in which the reagents are supplied are unsuitable for that purpose. The kits may either contain only a sufficient quantity of the reagent for a single test or larger amounts of reagents so that a number of tests can be performed.

The immunoassay of the present invention offers several advantages which are thought to be significant in this field. Prior enzyme immunoassays have required a specific enzyme-coupled reagent for each individual substance to be measured, and have required that prior to assay the antibody or analyte associated with the competitive or immuno-reaction must be covalently bound to the enzyme label. Our present method, however, has the advantage of allowing the use of the same enzyme-linking reagents (i.e., bridging second antibody and soluble immune complex reagents) for a variety of specific substances being assayed. Our method also obviates the more difficult covalent couplings of antigen or antibody to enzyme and the subsequent purification steps required by prior methods.

Further, the method of the present invention offers potential for greater sensitivity than prior art methods because higher ratios of enzymes to the first immunosorbent-analyte-antibody complex may be formed. For example, in the second step of the process, more than one molecule of the bridging antibody may bind to the immunosorbent/analyte/antibody complex, and more than one soluble immune complex of anti-enzyme/enzyme may bind per molecule of bridging antibody, and finally there may be more than one enzyme molecule per anti-enzyme molecule in the soluble immune complex. Therefore, it is conceivable that ratios of 5:1 or greater of enzyme to analyte/first antibody complex may be formed thus amplifying the procedure sensitivity.

The present immunoassay is applicable to the measurement of both low molecular weight analytes and high molecular weight analytes, whereas many other enzyme immunoassays are generally not suitable for both types of analytes. The analyte measured by the present method may in itself be an antibody; for example, conditions can be devised that allow for measurement of circulating human antibodies. Our method also is less susceptible to endogenous interferences or inhibitors in comparison to other methods in which the enzyme label contacts the specimen, in that the enzyme label (of the immune complex) is not introduced according to the present invention until after the soluble sample components are removed by washing to thereby eliminate the possibility of any sample interferences. The assay of the present invention, unlike certain other assays, does not require pure antibody, and commercial antisera (antibody) may be used in its practice. Various enzymatic activity measurement techniques may be used with the present assay as the activity of the enzyme can be measured either while the enzyme is bound to the immunosorbent or after being released from the immunosorbent. Furthermore, the present enzyme immunoassay can successfully compete with radioimmunoassay without the disadvantages of radioisotope labeling. Other advantages will be apparent to those skilled in the art upon review of the present disclosure.

We claim:

1. A competitive enzyme-linked immunoassay for soluble immunogen or hapten analyte in a sample solution including the steps of:
   (a) providing an insoluble solid immunosorbent to which analyte has been linked;
   (b) carrying out a competitive reaction between analyte in the sample solution and analyte linked to said solid immunosorbent for a selected quantity of a first antibody for the analyte;
   (c) coupling a heterologous bridging second antibody to any first antibody linked to analyte on the solid immunosorbent, the bridging second antibody being directed against the first antibody;
   (d) coupling a soluble antibody-enzyme immune complex to any bridging second antibody coupled to the first antibody linked to analyte on the immunosorbent, the antibody of the antibody-enzyme immune complex being of the same species as the first antibody or a cross-reactive species; and
   (e) measuring the activity of the enzyme coupled to the immunosorbent to indirectly determine the presence of the analyte in the sample.

2. A competitive enzyme-linked immunoassay for determining the concentration of soluble immunogen or hapten analyte in a sample solution comprising the steps of:
   (a) providing an insoluble solid immunosorbent to which the analyte has been linked;
   (b) forming a mixture of the sample solution suspected of containing the analyte, the insoluble solid immunosorbent having the analyte linked thereto and a selected quantity of first antibody for the analyte;
   (c) permitting a competitive reaction for the selected quantity of first antibody to proceed between the analyte linked to the immunosorbent and any analyte in the sample solution;
   (d) separating from said mixture the immunosorbent with any first antibody bound to analyte thereon;
   (e) adding to said separated immunosorbent with any first antibody bound to analyte thereon a heterologous bridging second antibody directed against the first antibody under conditions in which the second antibody will link to first antibody attached to analyte linked to the immunosorbent;
   (f) separating the immunosorbent with any first antibody bound to analyte thereon and bridging second antibody bound to any first antibody, and adding a soluble antibody-enzyme immune complex under conditions in which the immune complex will couple to bridging second antibody, the antibody of the antibody-enzyme immune complex being of the same species as the first antibody or a cross-reactive species;
   (g) separating the immunosorbent with any first antibody bound to analyte thereon, bridging second antibody bound to the first antibody, and soluble antibody-enzyme immune complex coupled to the bridging second antibody; and
   (h) measuring the activity of enzyme coupled to the immunosorbent to determine the concentration of any soluble immunogen or hapten analyte in the sample solution.

3. The method of claim 2 in which the enzyme activity is measured by first releasing enzyme from the immunosorbent and then determining the activity thereof.

4. The method of claim 2 in which the enzyme activity is measured while enzyme is coupled to the immunosorbent.

5. A competitive enzyme-linked immunoassay for determining the concentration of soluble immunogen or hapten analyte in a sample solution comprising the steps of:
   (a) providing an insoluble solid immunosorbent to which the analyte has been linked;
   (b) forming a mixture of a sample solution suspected of containing the analyte, the insoluble solid immunosorbent having the analyte linked thereto and a selected quantity of first antibody for the analyte;
   (c) permitting a competitive reaction for the selected quantity of first antibody to proceed between the analyte linked to the immunosorbent and any analyte in the sample solution;
   (d) separating from said mixture the immunosorbent with any first antibody bound to analyte thereon;
   (e) adding to said separated immunosorbent with any first antibody bound to analyte thereon a heterologous bridging second antibody directed against the first antibody under conditions in which the second antibody will link to first antibody attached to analyte linked to the immunosorbent;
   (f) separating the immunosorbent with any first antibody bound to analyte thereon and bridging second antibody bound to any first antibody, and adding a soluble anti-peroxidase/peroxidase immune complex under conditions in which the immune complex will couple to bridging second antibody, the anti-peroxidase of the immune complex being of the same species as the first antibody or a cross-reactive species;
   (g) separating the immunosorbent with any first antibody bound to analyte thereon, bridging second antibody bound to the first antibody, and soluble anti-peroxidase/peroxidase immune complex coupled to the bridging second antibody; and (h) measuring the activity of enzyme coupled to the immunosorbent to determine the concentration of any soluble immunogen or hapten analyte in the sample solution.

6. A competitive enzyme-linked immunoassay for soluble human choriogonadotropin (HCG) in a sample solution comprising the steps of:
(a) providing an insoluble solid immunosorbent to which HCG has been linked;
(b) forming a mixture of a sample solution suspected of containing HCG, the insoluble solid immunosorbent having HCG linked thereto and a selected quantity of rabbit anti-HCG first antibody for the HCG;
(c) permitting a competitive reaction for the selected quantity of said first antibody to proceed between the HCG linked to the immunosorbent and any HCG in the sample solution;
(d) separating from said mixture the immunosorbent with any HCG/rabbit anti-HCG bound thereto;
(e) adding to said separated immunosorbent with any HCG/rabbit anti-HCG bound thereto goat anti-rabbit immunoglobulin G (GARIgG) bridging second antibody under conditions in which the GARIgG will link to HCG/rabbit anti-HCG bound to the immunosorbent;
(f) separating the immunosorbent with any HCG/rabbit anti-HCG/GARIgG bound thereto, and adding a soluble rabbit anti-peroxidase/peroxidase (PAP) immune complex under conditions in which the PAP will couple to the GARIgG;
(g) separating the immunosorbent with any HCG/rabbit anti-HCG/GARIgG/PAP complex coupled thereto; and
(h) measuring the activity of the peroxidase of the immunosorbent to indirectly determine the concentration of HCG in the sample solution.

7. A competitive enzyme-linked immunoassay for soluble testosterone in a sample solution comprising the steps of:
(a) providing an insoluble solid immunosorbent to which testosterone has been linked;
(b) forming a mixture of a sample solution suspected of containing testosterone, the insoluble solid immunosorbent having testosterone linked thereto and a selected quantity of rabbit anti-testosterone first antibody for the testosterone;
(c) permitting a competitive reaction for the selected quantity of said first antibody to proceed between the testosterone linked to the immunosorbent and any testosterone in the sample solution;
(d) separating from said mixture the immunosorbent with any testosterone/rabbit anti-testosterone (T/rabbit anti-T) bound thereto;
(e) adding to said separated immunosorbent with any T/rabbit anti-T bound thereto goat anti-rabbit immunoglobulin G (GARIgG) bridging second antibody under conditions in which the GARIgG will link to T/rabbit anti-T bound to the immunosorbent;
(f) separating the immunosorbent with any T/rabbit anti-T/GARIgG bound thereto, and adding a soluble rabbit anti-peroxidase/peroxidase (PAP) immune complex under conditions in which the PAP will couple to the GARIgG;
(g) separating the immunosorbent with any T/rabbit anti-T/GARIgG/PAP complex coupled thereto; and
(h) measuring the activity of the peroxidase of the immunosorbent to indirectly determine the concentration of testosterone in the sample solution.

8. A kit for performing a competitive enzyme-linked immunoassay for the detection of a soluble suspected immunogen or hapten analyte in a sample solution, said kit comprising:
(a) a first antibody specific for said analyte;
(b) a solid immunosorbent having the analyte linked thereto which will compete with any of the analyte in a sample solution for the first antibody;
(c) a heterologous bridging second antibody directed against the first antibody and which will link to said first antibody; and
(d) a soluble antibody-enzyme immune complex which can couple to the bridging second antibody, the antibody of the antibody-enzyme immune complex being of the same species as the first antibody or a cross-reactive species so that the concentration of free analyte in solution can be determined by measurement of the enzymatic activity of enzyme coupled to the immunosorbent.

9. The kit of claim 8 which contains means for measuring the enzymatic activity of the enzyme of the soluble antibody-enzyme immune complex.

* * * * *